(12) United States Patent
Huene (10) Patent No.: US 6,419,700 B2
(45) Date of Patent: Jul. 16, 2002

(54) BONE PLUG ANCHORING DEVICE AND METHOD FOR ANCHORING ONE OR MORE TENDONS OR OTHER GRAFTS USING THE BONE PLUG ANCHORING DEVICE

(76) Inventor: Douglas B. Huene, 70 Stafford La., Suite 101-B, Delta, CO (US) 81416

(*) Notice: Subject to any disclaimer, the term of this patent is extended or adjusted under 35 U.S.C. 154(b) by 0 days.

(21) Appl. No.: 09/761,739

(22) Filed: Jan. 18, 2001

Related U.S. Application Data

(62) Division of application No. 09/174,550, filed on Oct. 19, 1998, now Pat. No. 6,235,058.

(51) Int. Cl.$^7$ .................................................. A61F 2/08
(52) U.S. Cl. ........................................ 623/13.14; 606/72
(58) Field of Search .......................... 623/13.13, 13.14, 623/13.15, 13.16; 606/72, 75, 151

(56) References Cited

U.S. PATENT DOCUMENTS

| | | | |
|---|---|---|---|
| 3,973,277 A | 8/1976 | Semple et al. ..................... 3/1 |
| 4,590,928 A | 5/1986 | Hunt et al. ..................... 128/92 |
| 4,744,793 A | 5/1988 | Parr et al. ..................... 623/13 |
| 4,755,183 A | 7/1988 | Kenna ........................... 623/13 |
| 4,834,752 A | 5/1989 | Van Kampen ............... 623/13 |
| 4,946,462 A | 8/1990 | Watanabe .................... 606/148 |
| 4,950,270 A | 8/1990 | Bowman et al. ............. 606/72 |
| 5,224,946 A | 7/1993 | Hayhurst et al. ............. 606/72 |
| 5,261,914 A | 11/1993 | Warren .......................... 606/73 |
| 5,268,001 A | 12/1993 | Nicholson et al. ............ 606/72 |
| 5,306,301 A | 4/1994 | Graf et al. ..................... 626/13 |
| 5,320,115 A | 6/1994 | Kenna ........................ 128/898 |
| 5,352,229 A | 10/1994 | Goble et al. ................. 606/72 |
| 5,372,599 A | 12/1994 | Martins ........................ 606/75 |
| 5,393,302 A | 2/1995 | Clark et al. ................. 623/13 |
| 5,425,766 A | 6/1995 | Bowald ........................ 623/13 |
| 5,425,767 A | 6/1995 | Steininger et al. ........... 623/13 |
| 5,472,452 A | 12/1995 | Trott ........................... 606/232 |
| 5,505,735 A | 4/1996 | Li ................................ 606/72 |
| 5,531,792 A | 7/1996 | Huene ......................... 623/16 |
| 5,571,104 A | 11/1996 | Li ................................ 606/72 |
| 5,575,819 A | 11/1996 | Amis ........................... 623/13 |
| 5,584,835 A | 12/1996 | Greenfield ................... 606/73 |
| 5,601,558 A | 2/1997 | Torrie et al. ................. 606/72 |
| 5,632,748 A | 5/1997 | Beck, Jr. et al. ............. 606/89 |
| 5,643,266 A | 7/1997 | Li ................................ 606/72 |
| 5,674,224 A | 10/1997 | Howell et al. ............... 606/88 |
| 5,702,397 A | 12/1997 | Goble et al. ................. 606/72 |
| 5,713,903 A | 2/1998 | Sander et al. ............... 606/72 |
| 5,720,753 A | 2/1998 | Sander et al. ............. 606/104 |
| 6,013,077 A | 1/2000 | Harwin ........................ 606/72 |

*Primary Examiner*—Bruce Snow
(74) *Attorney, Agent, or Firm*—Liniak, Berenato, Longacre & White, LLC (57) ABSTRACT

A bone plug anchoring device is provided for anchoring at least one graft to a bone. The bone plug anchoring devices comprises a plug and a locking element. The plug has a hollow passageway and a flange portion which extends radially out from the plug. The locking element is adapted to cooperate with the flange portion so that, when the locking element is locked to the flange portion while the graft(s) is (are) sandwiched between the locking element and the flange portion, the graft (or grafts) remains (or remain) anchored to the plug. The bone plug anchoring device is particularly well-suited for anchoring a hamstring tendon graft to a tibia after passing through a femur. The present invention also provides a method for anchoring at least one graft to a first bone. The method comprises the steps of: passing the graft(s) through a hollow passageway in a plug; securing the plug to a surface of the first bone through which the graft(s) passes (or pass); anchoring the graft(s) to the plug using a locking element which cooperates with a flange portion of the plug to lock the graft(s) between the locking element and the flange portion while the graft(s) is (are) sandwiched therebetween. The anchoring device and method are particularly well-suited for use on grafts, including but not limited to tendons (e.g., the hamstring tendon).

18 Claims, 6 Drawing Sheets

BONE PLUG ANCHORING DEVICE AND METHOD FOR ANCHORING ONE OR MORE TENDONS OR OTHER GRAFTS USING THE BONE PLUG ANCHORING DEVICE

This application is a divisional of application Ser. No. 09/174,550, filed Oct. 10, 1998 now U.S. Pat. No. 6,235,050.

BACKGROUND OF THE INVENTION

The present invention relates to a bone plug anchoring device which is securable to a bone where a tendon graft or other graft is to be anchored, and a method for anchoring one or more tendons or other grafts using the bone plug anchoring device.

There are several known devices which are capable of securing artificial ligaments and/or artificial tendons to bones. Some of those devices, however, are directed solely to artificial ligaments and/or tendons and may not be suitable for use in connection with grafts of natural tissue, such as an actual tendon.

While some devices are suitable for use on grafts of natural tissue, such devices tend to provide less than optimal results. Some merely squeeze or press the soft tissue against a surface of the bone. Since a bone surface is limited in its ability to frictionally retain the soft tissue, the soft tissue may slide with respect to the bone, especially if a significant amount of tension is placed on the soft tissue. The patient's activity therefore becomes very limited when such devices are used.

Since hamstring muscles can be very strong, it is important that any device which is used to secure hamstring tendon grafts to a bone be able to withstand significant amounts of tension without allowing slippage. Since muscles tend to deteriorate when not used, it is desirable that such devices be able to withstand such significant amounts of tension as soon as possible after implantation. This permits the patient to resume physical activity soon after surgery, thereby minimizing muscle deterioration.

There is consequently a need in the art for an anchoring device which is capable of securely anchoring a graft to bone, especially one which grips the graft, not by pressing it against a bone, but rather by pressing cooperating parts of the anchoring device against the graft while the graft is positioned therebetween, and which can be tightened sufficiently to withstand significant amounts of tension without slippage.

SUMMARY OF THE INVENTION

It is a primary object of the present invention to overcome at least some of the problems associated with prior art anchoring devices.

Another object of the present invention is to provide an anchoring device and method which are suitable for use with grafts, such as natural tendon grafts, in addition to being suitable for use with artificial ligaments and/or artificial tendons.

Yet another object of the present invention is to provide an anchoring device and method for securely anchoring a graft to a bone, especially one which grips the graft, not by pressing it against a bone, but rather by pressing cooperating parts of the anchoring device against the graft while the graft is positioned therebetween.

Still another object of the present invention is to provide an anchoring device and method which facilitate tightening of the anchoring device sufficiently to withstand significant amounts of tension without slippage.

To achieve these and other objects, the present invention provides a bone plug anchoring device for anchoring at least one graft to a bone. The bone plug anchoring device comprises a plug and a locking element. The plug has a hollow passageway and a flange portion which extends radially out from the plug. The locking element is adapted to cooperate with the flange portion so that, when the locking element is locked to the flange portion while the graft(s) is (are) sandwiched between the locking element and the flange portion, the graft (or grafts) remains (or remain) anchored to the plug. The bone plug anchoring device is particularly well-suited for anchoring a hamstring tendon graft to a tibia after passing through a femur.

The present invention also provides a method for anchoring at least one graft to a first bone. The method comprises the steps of: passing the graft(s) through a hollow passageway in a plug; securing the plug to a surface of the first bone through which the graft(s) passes (or pass); and anchoring the graft(s) to the plug using a locking element which cooperates with a flange portion of the plug to lock the graft(s) between the locking element and the flange portion while the graft(s) is (are) sandwiched therebetween.

Also provided by the present invention is a method for anchoring at least one hamstring tendon graft. The method comprises the steps of: creating a tibial tunnel through a patent's tibia, so that the tibial tunnel opens toward a femur of the patient; securing an anchoring element at the femur; passing the hamstring tendon graft(s) through the tibial tunnel and around the anchoring element and back through the tibial tunnel so that two portions of the hamstring tendon graft(s) extend out from an opening in the tibial tunnel which is directed away from the femur; securing a plug into the opening in the tibial tunnel, so that the two portions of each hamstring tendon graft extend through a hollow passageway in the plug; and anchoring the two portions of the hamstring tendon graft(s) to the plug using a locking element which cooperates with a flange portion of the plug to lock the two portions between the locking element and the flange portion while the two portions are sandwiched therebetween.

The above and other objects and advantages will become more readily apparent when reference is made to the following description taken in conjunction with the accompanying drawings.

DESCRIPTION OF PREFERRED EMBODIMENTS

Figure 1:
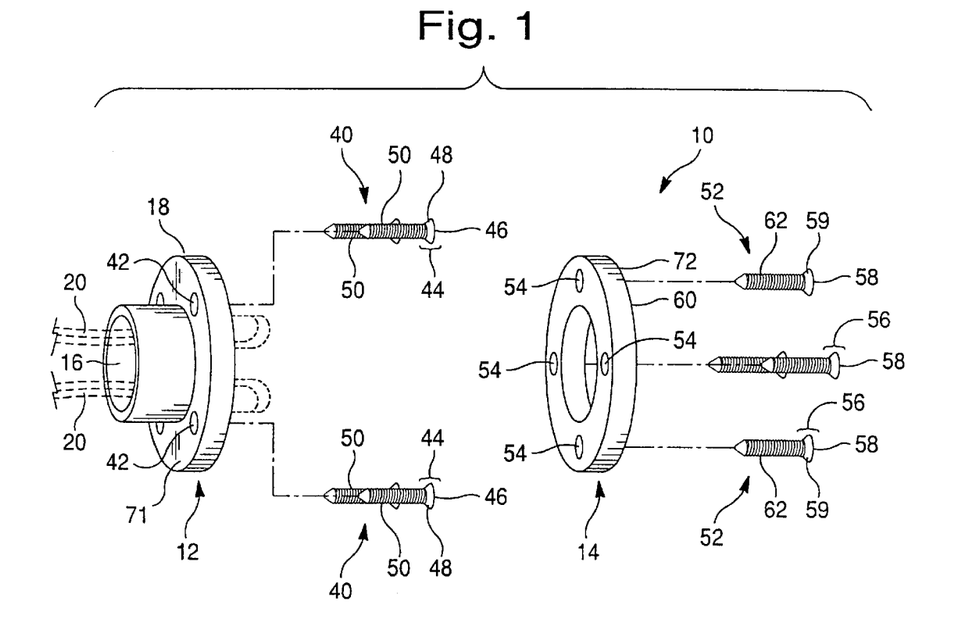
FIG. 1 is an exploded perspective view of an anchoring device according to a preferred embodiment of the present invention.
Figure 2:
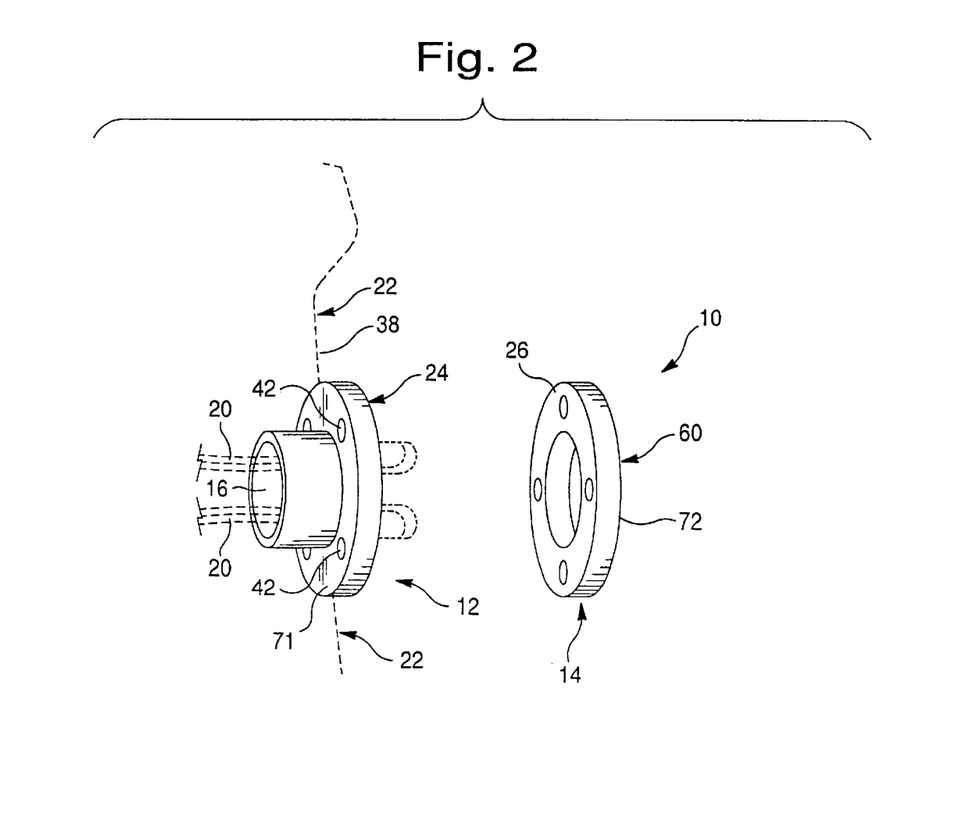
FIG. 2 is an exploded perspective view of the anchoring device shown in FIG. 1, also showing a bone to which the anchoring device can be fastened.

FIGS. 1 and 2 show a bone plug anchoring device 10 according to a preferred embodiment of the present invention. The bone plug anchoring device 10 is capable of anchoring at least one graft 20 (e.g., a tendon) to a bone 22.

The bone plug anchoring device 10 comprises a plug 12 and a locking element 14. The plug 12 has a hollow passageway 16 and a flange portion 18 which extends radially out from the plug 12. The locking element 14 is adapted to cooperate with the flange portion 18 so that, when the locking element 14 is locked to the flange portion 18 while the graft(s) 20 is (are) sandwiched between the locking element 14 and the flange portion 18, the graft (or grafts) 20 remains (or remain) anchored to the plug 12.

As shown in FIGS. 1 and 2, both the plug 12 and the flange portion 18 have an annular shape. The locking element 14 also has an annular shape, and preferably, one which substantially matches the annular shape and dimension of the flange portion 18. It is understood, however, that the present invention is not limited to such annular arrangements. The locking element 14, for example, can be shaped so that it extends around only part of the circumference of the hollow passageway 16. Similar non-annular arrangements can be implemented in connection with the flange portion 18 and/or the plug 12. Thus, among the plug 12, flange portion 18, and locking element 14, none is limited to having a complete annular shape.

Since the anchoring device 10 is designed for implantation in a bone 22, it preferably is constructed of biocompatible material, such as titanium, stainless steel, and the like.

Figure 3:
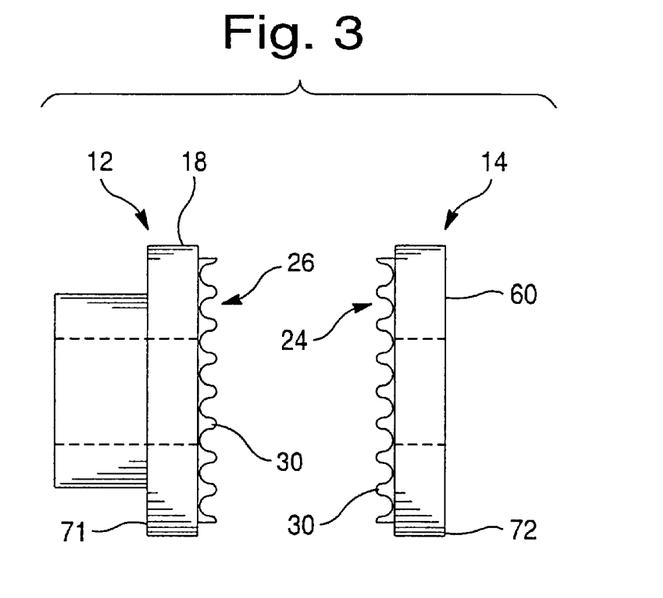
FIG. 3 is an exploded side view of an alternative embodiment of the anchoring device shown in FIGS. 1 and 2.

As shown in FIG. 3, the flat surfaces 24,26 of the locking element 14 and flange portion 18 which engage the graft 20 can be modified to provide surface relief 30. While the surface relief 30 can be provided on either one of the flange portion 18 and the locking element 14, it preferably is provided on both. The surface relief 30 is arranged so as to engage and more positively grip the graft(s) 20 when the graft(s) 20 is (are) sandwiched between the flange portion 18 and the locking element 14. The surface relief 30 thereby enhances anchoring of the graft(s) 20 in position.

Figure 4:
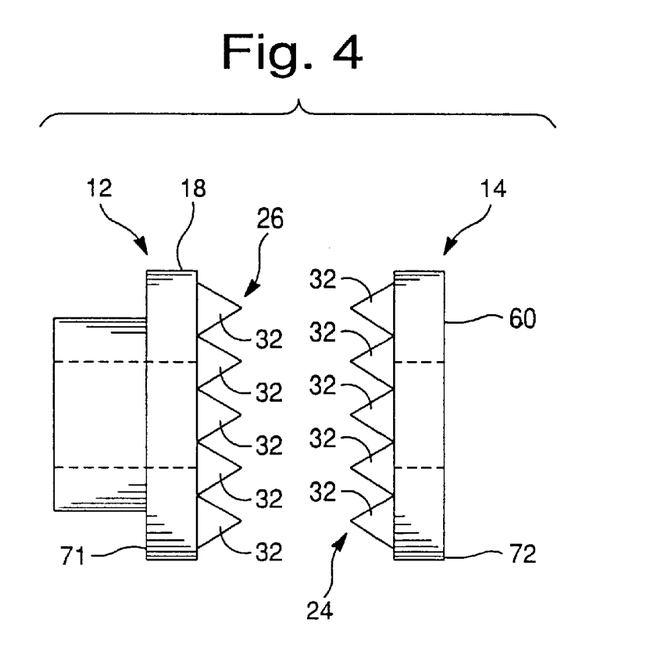
FIG. 4 is an exploded side view of another alternative embodiment of the anchoring device shown in FIGS. 1 and 2.
Figure 5:
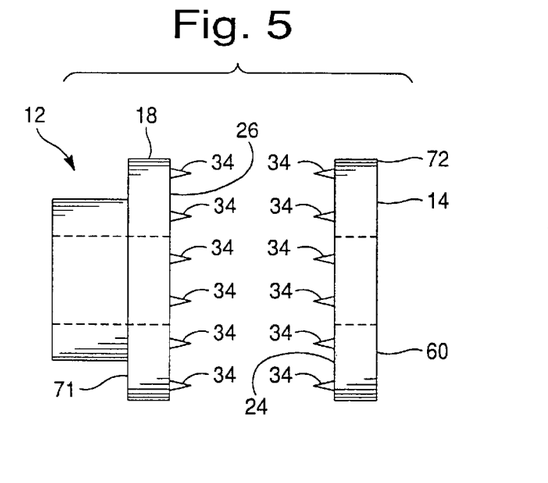
FIG. 5 is an exploded side view of yet another alternative embodiment of the anchoring device shown in FIGS. 1 and 2.
Figure 6:
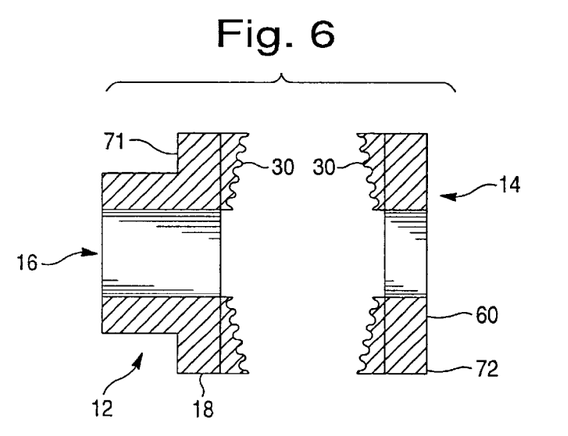
FIG. 6 is an exploded cross-sectional view of still another alternative embodiment of the anchoring device shown in FIGS. 1 and 2.

The surface relief 30 can be provided with different relief configurations. FIG. 3, for example, shows undulations 30 on the surfaces 24,26. FIG. 4 shows a relief configuration which includes teeth 32. Still another relief configuration involves the use of spikes 34, as illustrated in FIG. 5. Any of the foregoing and other configurations can be arranged so that anchoring of the graft(s) 20 is progressively tighter toward radially outer portions of the flange portion 18. As shown in FIG. 6, the undulations 30, for example, can be graded so that the grip on the graft(s) 20 is tighter toward the periphery of the flange portion 18. While the exemplary relief configurations shown in the drawings provide favorable gripping of the graft(s) 20, it is understood that the invention is not limited to the illustrated relief configurations.

Figure 7:
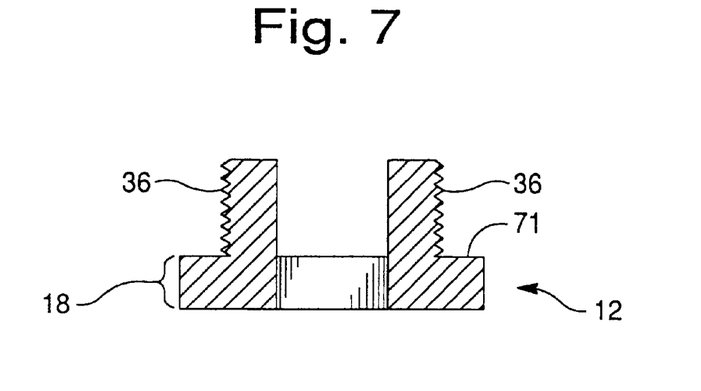
FIG. 7 is a cross-sectional view of a plug according to an alternative embodiment of the anchoring devices shown in FIGS. 1–6.

As shown in FIG. 7, the plug 12 can be provided with external threads 36 to facilitate screwing of the plug 12 into the bone 22. Preferably, the external threads 36 of the plug 12 are graded so that progressive advancement of the plug 12 into the bone 22 causes progressive tightening of the plug 12 into the bone 22. Such grading can be implemented, for example, using a configuration similar to that of a graded wood screw.

If the graft(s) 20 are inserted prior to the plug 12 so that they extend out through the bone 22, the externally threaded version of the plug 12 can be advanced into the bone 22 using a cannulated screw driver which is hollow to accommodate the graft(s) 20 during insertion of the plug 12.

Figure 8:
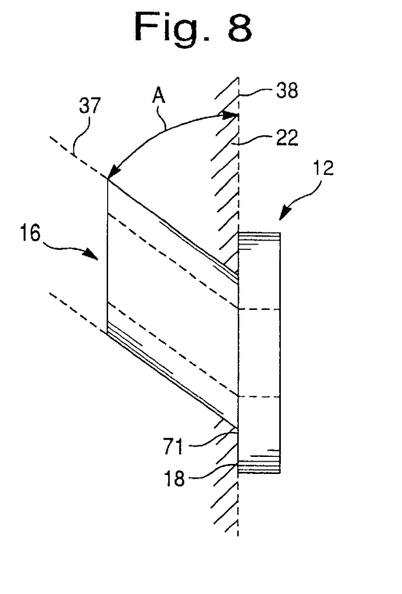
FIG. 8 is a side view of a plug according to an alternative embodiment of the anchoring devices shown in FIGS. 1–7.

In some situations, such as the grafting of a hamstring tendon to the femur and tibia of a patient, it is desirable to have the grafts 20 (e.g., tendons) extend through a tunnel 37 in the bone 22, which tunnel 37 is non-orthogonal with respect to the surface 38 of the bone 22 where the graft 20 enters, as best shown in FIG. 8.

Therefore, as shown in FIG. 8, the flange portion 18 can be angled so that it extends radially out from the plug 12 in a non-orthogonal direction with respect to the passageway 16. The non-orthogonal direction corresponds to the angle A between the tunnel 37 and the surface 38 of the bone 22 where the plug 12 is to be received. This arrangement advantageously allows the passageway 16 to extend partially into the tunnel 37 while the flange portion 18 remains flush with the surface 38 of the bone 22.

Preferably, the flange portion 18 of the plug 12 is fastened to the bone 22 using a suitable fastening mechanism. As shown in FIG. 1, the fastening mechanism can include a set of bone screws 40 and respective holes 42 in the flange portion 18. Two of the holes 42 are not visible in FIG. 1. The bone screws 40 are inserted through the holes 42 and are threadedly received in the bone 22. The bone screws 40 preferably have frustoconical heads 44 which present a flat top surface 46 and a circumferential outer surface 48. The diameter of each hole 42 is largest close to the surface 26 and progressively decreases until it reaches or comes very close to the diameter of the threads 50. This progressive reduction in diameter provides a shoulder (not shown) in each of the holes 42 which bears against the circumferential outer surface 48 of the frustoconical head 44 as each screw 40 is tightened into the bone 22. Preferably, the heads 44 are sized so that the flat top surface 46 is flush with the surface 26 of the flange portion 18 whenever the shoulder bears against the outer surface 48.

While FIGS. 1 and 7 show exemplary embodiments in which the fastening mechanism involves threaded engagement of the plug 12 to the bone 22, it is understood that alternative fastening mechanisms, such as pins, can be used. The present invention thus is not limited to the illustrated fastening mechanisms.

A securement mechanism preferably is provided for securing the locking element 14 to the flange portion 18. As illustrated in FIG. 1, the securement mechanism may include a set of securement bolts 52, respective holes 54 in the locking element 14, and respective threaded holes (not shown) in the flange portion 18. The securement bolts 52 are inserted through the holes 54 and are threadedly received in the threaded holes of the flange portion 18. The securement bolts 52 preferably have frustoconical heads 56 which present a flat top surface 58 and a circumferential outer surface 59. The diameter of each hole 54 is largest close to the outside surface 60 of the locking element 14 and progressively decreases until it reaches or comes very close to the diameter of the threads 62. This progressive reduction in diameter provides a shoulder (not shown) in each of the holes 54 which bears against the circumferential outer surface 59 of the frustoconical head 56 as each bolt 52 is tightened into the flange portion 18. Preferably, the heads 56 are sized so that the flat top surface 58 is flush with the outside surface 60 of the flange portion 18 whenever the shoulder bears against the circumferential outer surface 59 of the head 56.

While the securement mechanism in the preferred embodiment utilizes threaded couplers, it is understood that the invention is not limited to such couplers. There are many different kinds of securement mechanisms, with or without threaded couplers, which can be used to secure the locking mechanism in place.

Preferably, the locking element 14 is unlockable to facilitate subsequent re-tensioning of the graft(s) after initial anchoring thereof. In the illustrated embodiment, for example, the securement bolts 52 can be unscrewed to loosen the locking element 14. The graft(s) 20 (e.g., tendons) then can be pulled to provide a desired adjustment of the tension in the graft(s) 20. After the desired amount of tension is achieved, the locking element 14 is re-locked by turning the bolts 52 in a tightening direction.

Figure 9A:
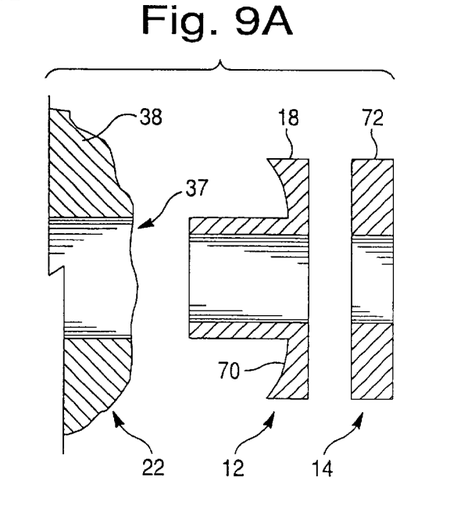
FIG. 9A is a cross-sectional view of an alternative embodiment of the anchoring devices shown in FIGS. 1–8.

As shown in FIG. 9A, an alternative embodiment of the flange portion 18 may include a contoured bone-engaging surface 70 which is contoured to substantially match the surface 38 of the bone 22 where the plug 12 is to be received. The embodiment illustrated in FIG. 9A also can be combined with any one of the features shown in FIGS. 1–8 or a combination thereof.

Figure 9B:
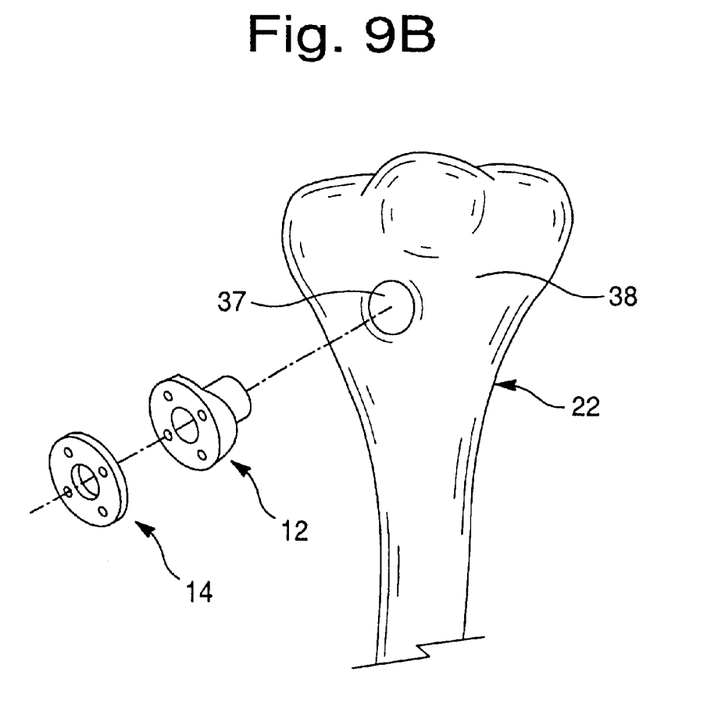
FIG. 9B is perspective view of another alternative embodiment of the anchoring devices shown in FIGS. 1–8.

In FIG. 9A, the only contoured portion of the plug 12 is the bone-engaging surface 70. It is often desirable, however, to minimize the profile of the combined plug 12 and locking element 14. In this regard, as shown in FIG. 9B, the entire flange portion 18 and the entire locking element 14 can be contoured in a manner which matches the contour of the bone surface 38. The resulting arrangement provides a much smaller profile and advantageously minimizes the feel and appearance of deformities on the bone.

The bone-engaging surface 70 or 71 of any of the flange portions 18 illustrated in FIGS. 1–8, 9A and 9B can be roughened or otherwise modified to provide a more stable plug-to-bone contact area. Such surface roughening or other modifications can be provided regardless of whether the bone-engaging surface is contoured.

While the locking elements 14 shown in FIGS. 1–8, 9A, and 9B have a rather abrupt edge 72 around the periphery of each surface 60, it is understood that this edge 72 can be rounded or reduced to provide a curvature with a more natural feel and appearance.

Figure 9C:
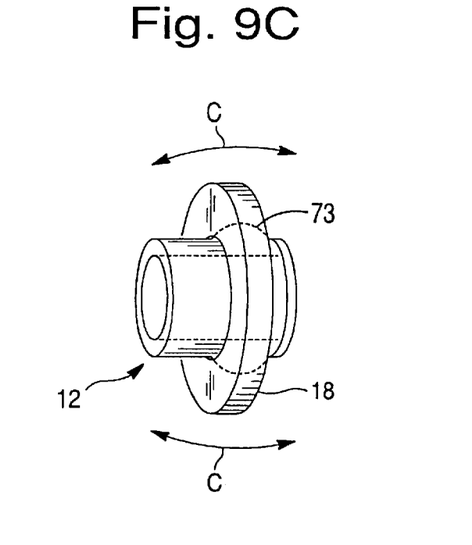
FIG. 9C is a perspective view of yet another alternative embodiment of the anchoring devices shown in FIGS. 1–8, 9A, and 9B.

As shown in FIG. 9C, the flange portion 18 can be carried by the plug 12 wit play between the flange portion 18 and the plug 12. This play can be rotational and/or pivotal. In FIG. 9C, both rotational and pivotal play are provided using a ball-and-socket arrangement 73.

Pivotal mounting of the flange portion 18 is particularly useful when both external threads 36 (as shown in FIG. 7) and an angled flange portion 18 (as shown in FIG. 8) are desired on the same plug 12. It advantageously allows the flange portion 18 to pivot (indicated by arrows C) with respect to the rest of the plug 12. This pivoting, in turn, facilitates complete screwing of the plug 12 into an angled tunnel 37 of a bone 22 (as shown in FIG. 8), by allowing the flange portion 18 to remain parallel to the surface 38 of the bone 22 as the plug 12 is turned.

The ball-and-socket arrangement 73 also advantageously permits rotation of the flange portion 18 with respect to the rest of the plug 12. Thus, when the plug 12 has external screws 36 (as shown in FIG. 7) and the flange portion 18 and/or locking element is (are) contoured or carry a contoured bone-engaging surface 70 (as shown in FIGS. 9A and 9B), the flange portion 18 is allowed to rotate with respect to the rest of the plug 12 so that its contouring remains aligned with the matching contour of the bone surface 38.

While the ball-and-socket arrangement 73 provides significant advantages, it is understood that the present invention is not limited to that type of pivotal mounting. Other pivotal arrangements will suffice. Nor is the present invention limited to the illustrated ball-and-socket arrangement 73 for purposes of providing a rotatable mounting of the flange portion 18 to the rest of the plug 12. Other rotation-permitting mountings will suffice. In addition, it should be understood that the pivotal and/or rotational mounting of the flange portion 18 to the rest of the plug 12 can be combined with any one or any combination of the features shown in FIGS. 1–9B.

Preferably, the hollow passageway 16 has dimensions sufficient to accommodate not only the graft(s) 20 to be anchored, but also grafts of bone material. This way, bone material can be inserted into the hollow passageway 16 before, during, or after implantation of the plug 12.

The present invention also provides a method of anchoring at least one graft 20 (preferably two bone grafts) to a bone 22. While a preferred implementation of the method utilizes the bone plug anchoring device 10, it is understood that the inventive method is not limited to use with such an anchoring device.

According to the preferred implementation, the graft(s) 20 to be anchored is (are) passed through the hollow passageway 16 in the plug 12. The plug 12 then is secured to the surface 38 of the bone 22 through which the graft(s) 20 passes (pass), and the locking element 14 is used to anchor the graft(s) 20 to the plug 12. The locking element 14 cooperates with the flange portion 18 of the plug 12 to lock the graft(s) 20 between the locking element 14 and the flange portion 18 while the graft(s) is (are) sandwiched therebetween.

The steps which define the foregoing method can be performed in any desired order. The particular order used will be determined by, among other things, the location of the graft(s) 20, the type of graft being anchored, the amount of tension which is desirable on the graft 20, and the like.

Preferably, the graft 20 comprises at least one tendon, and the method further comprises a step of passing the tendon(s) through a tunnel 37 in the bone 22.

If the graft(s) is (are) to connect two bones, the method also may include the step of feeding the graft(s) 20 through a tunnel 37 in a first bone, to the second bone, and back through the first bone, prior to anchoring the graft(s) 20 to the plug 12. The plug 12, in turn, is fastened to the first bone. Preferably, the connection to the second bone is made by looping the graft(s) 20 around an anchoring element. The anchoring element may be part of the second bone, or alternatively, may be a prosthetic anchoring element which is implanted on or into the second bone.

While the step of anchoring the graft(s) 20 to the plug 12 can be performed in a permanent manner, a preferred implementation of the method is performed so that the locking element 14 remains unlockable to facilitate subsequent re-tensioning of the graft(s) 20.

Since the plug 12 can be provided with a contoured bone-engaging surface 70 on its flange portion 18, the step of securing the plug 12 to the surface of the first bone preferably includes the step of orienting the plug 12 so that the contoured bone-engaging surface 70 of the flange portion 18 substantially matches a contour of the surface of the first bone.

The bone plug anchoring device 10 and the aforementioned method are particularly well-suited for anchoring a hamstring tendon graft to a tibia after passing the raft through a femur. It is understood, however, that the invention is not limited to such use.

Figure 10:
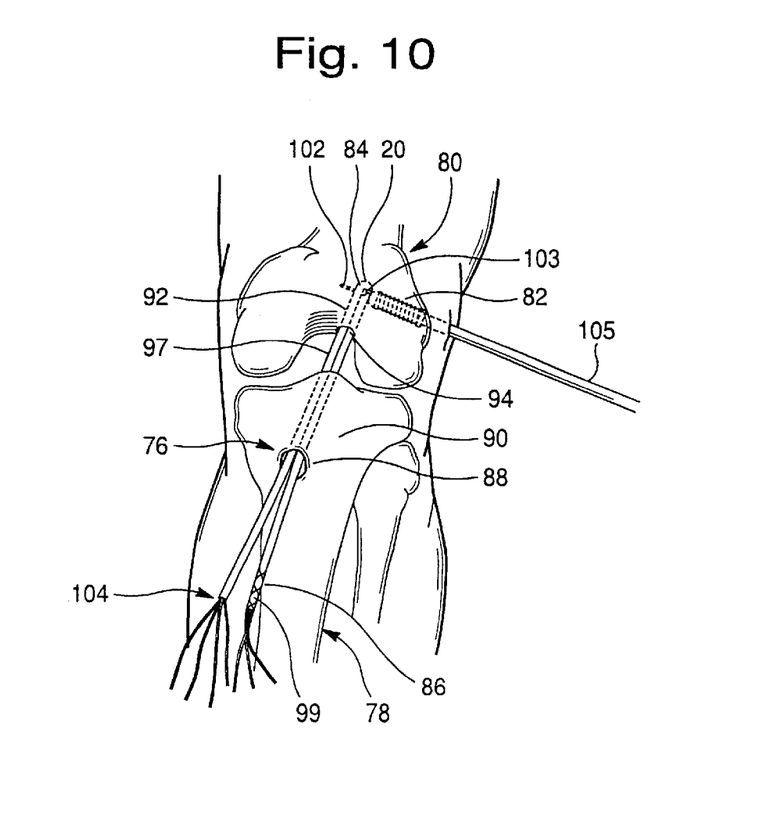
FIG. 10 is a perspective view of a human knee into which a graft is being anchored according to a preferred method of the present invention.
Figure 11:
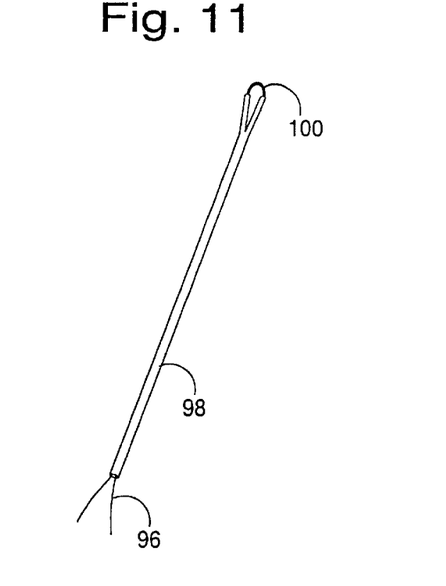
FIG. 11 is a perspective view of a looping tool for use in performing the preferred method.
Figure 12:
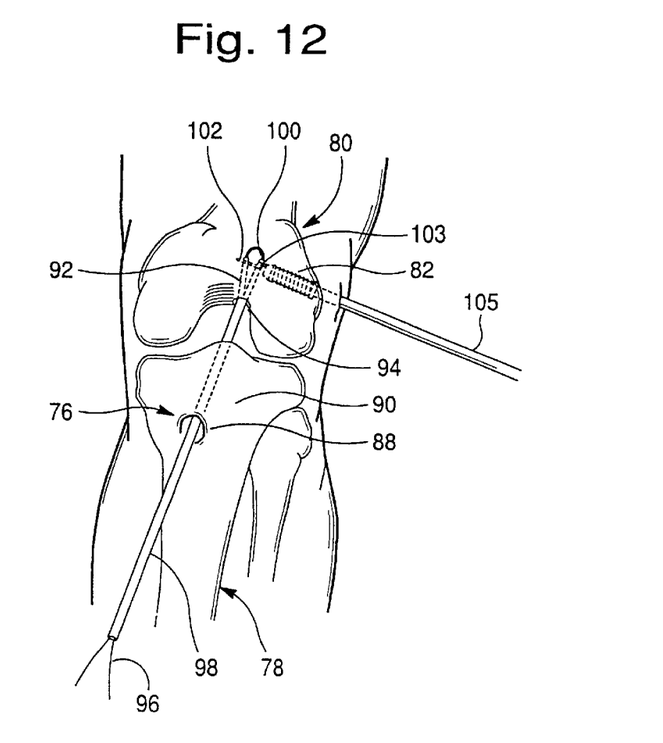
FIG. 12 is a perspective view of the human knee shown in FIG. 10, at an earlier stage in the preferred method.

As shown in FIGS. 10–12, the method of the present invention preferably includes the step of creating a tibial tunnel 76 through a patient's tibia 78 so that the tibial tunnel 76 opens toward a femur 80 of the patient. An anchoring element 82 is secured in the femur 80 and preferably is externally threaded to permit advancement of the anchoring element 82 transversely through the femur.

A hamstring tendon graft 20 (containing one or more tendons or individual grafts) is passed through the tibial tunnel 76 and around the anchoring element 82 and back through the tibial tunnel 76 so that two portions 84,86 of the hamstring tendon graft 20 extend out from an opening 88 in the tibial tunnel 76 which is directed away from the femur 80.

The plug 12 is secured into the opening 88 in the tibial tunnel 76 so that the two portions 84,86 of the hamstring tendon graft 20 extend through the hollow passageway 16 of the plug 12. The two portions 84,86 then are anchored to the plug 12 using the locking element 14. More specifically, the locking element 14 cooperates with the flange portion 18 of the plug 12 to lock the two portions 84,86 of the graft 20 between the locking element 14 and the flange portion 18 while the two portions 84,86 are sandwiched therebetween. Preferably, such anchoring of the graft 20 to the plug 12 is performed so that the locking element 14 remains unlockable. This, in turn, facilitates subsequent unlocking of the locking element 14 and re-tensioning of the hamstring tendon graft 20.

The step of securing the plug 12 into the opening 88 in the tibial tunnel 76 preferably includes the step of orienting the plug 12 so that a contoured bone-engaging surface 70 of the flange portion 18 substantially matches a contour of the tibia's surface 90. Such matching of the contours advantageously maximizes the bone-to-plug contact and can be used to provide an anchoring scheme which has a low overall profile after implantation. The flange portion 18 preferably is secured to the surface 90 of the tibia 78 using a fastening mechanism, such as the bone screws 40 and holes 42 shown in FIG. 1.

As shown in FIG. 10, a femoral tunnel 92 may be provided at least partially through the femur 80. The femoral tunnel 92 preferably has an opening 94 directed toward the tibia 78.

With reference to FIG. 11, a preferred method of placing the graft 20 around the anchoring 82 is performed using a suture 96 and a looping tool 98. Preferably, the suture is a 24 inch, monofilament, 1–0 suture. It is understood, however, that other suture types and sizes can be used.

The suture 96 is fed through the looping tool 98 to form a suture loop 100. Once the suture loop 100 has been established, the looping tool 98 can be used to feed the suture loop 100 into the opening 88 of the tibial tunnel 76 and then completely through the tibial tunnel 76. Insertion of the looping tool 98 continues into the femoral tunnel 92 until the suture loop 100 reaches a predetermined location in the femoral tunnel 92, where the anchoring element 82 is to be positioned.

The exemplary anchoring element 82 shown in FIGS. 10 and 12 is a bone mulch screw which is driven into the femur 80 so that it extends transversely through the femoral tunnel 92 and through the suture loop 100 contained therein. The suture loop 100 therefore extends around the anchoring element 82. With the suture loop 100 around the anchoring element 82, the anchoring element 82 is further advanced into the femur so that a tip 102 of the anchoring element 82 becomes imbedded in the femur 80, preferably about 2 to 3 millimeters beyond the femoral tunnel 92. The loop 100 therefore cannot slip past the anchoring element 82.

Advancement of the anchoring element 82 preferably is terminated when penetration of the tip 102 falls within the desired range of 2 to 3 millimeters and the bend 103 which connects the tip 102 to the rest of the anchoring element 82 is oriented as shown in FIG. 10. This orientation of the bend 103, when tension is applied to the graft 20, advantageously tends to keep the graft 20 on the tip 102 and generally away from the wall of the tunnel 92 which is closest to the rest of the anchoring element 82. The orientation can be visually monitored by placing an appropriate indicator (e.g., a notch, symbol, and the like) on the driver tool 105 which drives the anchoring element 82 and by configuring the heads of the anchoring element 82 and driver tool 105 so that the anchoring element 82 can be driven by the driver tool 105 only when the driver tool 105 is in a predetermined rotational alignment with the anchoring element 82. This way, turning of the anchoring element 82 is possible only when the indicator on the driver tool 105 indicates the true orientation of the bend 103.

Next, a posterior end 104 of the suture 96 is attached to the hamstring tendon graft 20, as shown in FIG. 10. The anterior end (not shown) of the suture 96 then is pulled so that the posterior end 104 of the suture 96 and the hamstring tendon graft 20 are drawn into the tibial tunnel 76, then into the femoral tunnel 92, around the anchoring element 82, then back through the femoral tunnel 92, and back through the tibial tunnel 72 until the two portions 84,86 of the hamstring tendon graft 20 extend out from the opening 88 in the tibial tunnel 76. Preferably, whip stitches 97,99 are provided at the opposite ends of the graft 20 to facilitate connection to the suture 96 and passage through the tibial and femoral tunnels 76 and 92.

If the graft 20 is comprised of more than one individual graft (e.g., a semitendinosus graft and a gracilis graft) and the graft 20 hangs-up during attempts to pass it through the tibial and femoral tunnels 76,92, the graft 20 can be backed out and the individual grafts contained therein can be pulled through independently of one another. Preferably, the narrower graft(s) (e.g., the gracilis graft) is (are) pulled through after the other graft(s) (e.g., the semitendinosus graft). When two individual grafts make up the graft 20, it will be appreciated that the bending of the two individual grafts around the anchoring element 82 provides a total of four graft strands extending through the plug 12.

The plug 12 can be applied to the tibia 80 before, during, or after passage of the graft 20 through the tibia 78 and femur 80. Regardless of when the plug 12 is applied, the tendon graft 20 is fed through the passageway 16 until both portions 84,86 extend out through the opening 88 an approximately equal distance. If one of the portions 84,86 extends farther out than the other, the other of the two portions 84,86 can be pulled until symmetry is achieved.

Once symmetry is achieved, both portions 84,86 are pulled to provide a physiologically appropriate amount of tension on the hamstring tendon graft 20. If the whip stitches 97,99 are provided, such pulling can be achieved by pulling on the whip stitches 97,99.

The locking element 14 then is used to anchor the tendon graft 20 in place, while the appropriate amount of tension continues to be applied. Once the locking element 14 is locked, the tendon graft 20 remains under the appropriate amount of tension and is prevented from slipping out of this tensioned condition by the locking element 14.

The tension on the graft 20 tends to urge the flange portion 18 and the locking element 14 against the bone 22. To some extent, therefore, this tension simplifies or eliminates the need for a fastening mechanism. An orientation preserving mechanism, for example, can be used instead of the fastening mechanism to prevent rotation of the plug 12. An example of such an orientation preserving mechanism is a single one of the bone screws 40 and a single one of the holes 42. The plug 12 cannot rotate when the single bone screw 40 passes through the hole 42 and becomes imbedded in the tibia 78.

Notably, the anchoring device 10 grips the graft 20, not by pressing it against a bone, but rather by squeezing the graft 20 between cooperating parts of the anchoring device 10 (e.g., the flange portion 18 and the locking element 14). The device and method of the present invention therefore provide a more positive grip on the graft 20 and are better able to prevent slippage thereof, even if a significant amount of tension is applied to the graft 20. The patient therefore can resume physical activity immediately, with little or no need for rehabilitation. This represents a significant advance over prior techniques and anchoring devices, especially those which press the graft into a bone.

The anchoring device 10 and method advantageously can be used to anchor grafts, such as natural tendons, in addition to being suitable for use with prosthetic implants, such as artificial ligaments and/or artificial tendons.

Since the grip provided by the locking element 14 squeezing the graft 20 against the flange portion 18 can be selectively tightened by merely tightening the locking element 14, the anchoring device 10 and method of the present invention are readily adaptable to withstand different and significant amounts of tension without slippage.

While this invention has been described as having a preferred design, it is understood that the invention is not limited to the illustrated and described features. To the contrary, the invention is capable of further modifications, usages, and/or adaptations following the general principles of the invention and therefore includes such departures from the present disclosure as come within known or customary practice in the art to which the invention pertains, and as may be applied to the central features set forth above, and which fall within the scope of the appended claims.

What is claimed is:

1. A method for anchoring at least one graft to a first bone, said method comprising the steps of:

passing at least one graft through a longitudinally extending hollow passageway in a plug having a periphery and a flange extending radially out from the plug periphery;

securing the plug to a surface of a first bone through which the at least one graft passes; and securing the at least one graft to the plug using a locking element which cooperates with the flange wherein the at least one graft extends from the hollow passageway and is sandwiched between the locking element and the flange.

2. The method of claim 1, wherein the at least one graft comprises at least one tendon, and wherein said method further comprises a step of passing the at least one tendon through a tunnel in the first bone.

3. The method of claim 1, further comprising the step of:

feeding the at least one graft through a tunnel in the first bone, to a second bone, and back through the first bone, prior to said step of securing the at least one graft to the plug.

4. The method of claim 3, wherein said step of feeding the at least one graft includes the step of looping the at least one graft around an anchoring element in the second bone.

5. The method of claim 1, wherein said step of securing the plug to the surface of the first bone comprises the step of fastening the flange to the surface of the first bone using a fastening mechanism.

6. The method of claim 1, wherein said step of securing the at least one graft to the plug is performed so that the locking element remains unlockable to facilitate subsequent re-tensioning of the at least one graft.

7. The method of claim 1, wherein said step of securing the plug to the surface of the first bone further comprises the step of orienting the plug so that a contoured bone-engaging surface of the flange substantially matches a contour of the surface of the first bone.

8. The method of claim 1, wherein said step of securing the plug to a surface of a first bone further comprises the step of roughening a bone-engaging surface of the flange prior to securing the plug to the surface of the first bone.

9. The method of claim 1, wherein said step of securing the plug to a surface of a first bone comprises the step of securing the flange to the surface of the first bone using an orientation preserving mechanism for preventing rotation of the plug.

10. A method for anchoring at least one hamstring tendon graft, said method comprising the steps of:

creating a tibial tunnel through a patient's tibia, so that the tibial tunnel opens toward a femur of the patient;

securing an anchoring element at the femur;

passing at least one hamstring tendon graft through the tibial tunnel and around the anchoring element and back through the tibial tunnel so that two portions of the at least one hamstring tendon graft extend out from an opening in the tibial tunnel which is directed away from the femur;

securing a plug into the opening in the tibial tunnel, the plug having a longitudinally extending hollow passageway, a periphery and a flange extending radially out from the plug periphery;

passing the two portions of each hamstring tendon graft through the hollow passageway; and securing the two portions of the at least one hamstring tendon graft to the plug using a locking element which cooperates with a flange wherein the two portions extend from the hollow passageway and are sandwiched between the locking element and the flange.

11. The method of claim 10, wherein said step of securing the plug into the opening in the tibial tunnel comprises the step of fastening the flange to a surface of the tibia using a fastening mechanism.

12. The method of claim 10, wherein said step of securing the two portions of the at least one hamstring tendon graft to the plug is performed so that the locking element remains unlockable to facilitate subsequent re-tensioning of the two portions of the at least one hamstring tendon graft.

13. The method of claim 10, wherein said step of securing the plug into the opening in the tibial tunnel further comprises the step of orienting the plug so that a contoured bone-engaging surface of the flange substantially matches a contour of the surface of the first bone.

14. The method of claim 10, wherein said steps of securing an anchoring element at the femur; and passing at least one hamstring tendon graft through the tibial tunnel and around the anchoring element and back through the tibial tunnel, include the step of:

creating a femoral tunnel in the femur having a femoral tunnel opening directed toward the tibia;

providing a suture with a suture loop;

passing the suture loop into the opening in the tibial tunnel, through the tibial tunnel and into the femoral tunnel;

inserting the anchoring element through the femur so that it extends transversely through the femoral tunnel and through the suture loop contained therein, whereby the suture loop extends around the anchoring element;

attaching the at least one hamstring tendon graft to a first end of the suture; and pulling an opposite end of the suture so that the first end of the suture and the at least one hamstring tendon graft are drawn into the tibial tunnel, into the femoral tunnel, around the anchoring element, back through the femoral tunnel, and back through the tibial tunnel until the two portions of the at least one hamstring tendon graft extend out from the opening in the tibial tunnel.

15. The method of claim 14, further comprising the steps of:

unlocking the locking element subsequent to an initial anchoring of the graft; and re-tensioning the graft.

16. The method of claim 10, wherein said step of creating a tibial tunnel through a patient's tibia comprises the step of creating an angled tunnel into the tibia with respect to a tibia surface.

17. The method of claim 16, further comprising the step of mounting a pivotally operable plug, wherein the flange pivots with respect to the hollow passageway and the flange remains parallel to the tibia surface as the plug is inserted into the tibial tunnel.

18. The method of claim 10, further comprising the step of inserting a bone graft material into the hollow passageway, wherein the hollow passageway can accommodate the two portions of tendon graft and the bone graft material.

\* \* \* \* \*